US010316369B2

(12) United States Patent
Bachlava et al.

(10) Patent No.: US 10,316,369 B2
(45) Date of Patent: Jun. 11, 2019

(54) METHODS AND ASSAYS FOR MALE STERILE WATERMELON

(71) Applicant: Seminis Vegetable Seeds, Inc., St. Louis, MO (US)

(72) Inventors: Eleni Bachlava, Fairfield, CA (US); Tarek Joobeur, Sacramento, CA (US); Gregory E. Tolla, Woodland, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 35 days.

(21) Appl. No.: 14/733,767

(22) Filed: Jun. 8, 2015

(65) Prior Publication Data

US 2016/0130670 A1 May 12, 2016

Related U.S. Application Data

(60) Provisional application No. 62/018,413, filed on Jun. 27, 2014.

(51) Int. Cl.
| | |
|---|---|
| *A01H 5/10* | (2018.01) |
| *C12Q 1/6895* | (2018.01) |
| *A01H 5/08* | (2018.01) |
| *C12N 15/82* | (2006.01) |
| *A01H 1/04* | (2006.01) |

(52) U.S. Cl.
CPC ............ *C12Q 1/6895* (2013.01); *A01H 1/04* (2013.01); *A01H 5/08* (2013.01); *C12N 15/8289* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 2013/0055466 A1 | 2/2013 | Juarez et al. |
| 2013/0160154 A1* | 6/2013 | Tolla ............. A01H 5/08 800/260 |
| 2014/0041078 A1 | 2/2014 | Bachlava et al. |

OTHER PUBLICATIONS

Zhang et al., "Cytological Expression in the Mail-Sterile ms Mutant in Watermelon," *Journal of Heredity* 85(4):279-285, 1994.
Zhang et al., "Development of Genic Mail-sterile Watermelon Lines with Delayed-green Seedling Marker," *HortScience* 31(1):123-126, 1996.
Sandlin, "Genetic Mapping in Citrullus Lanatus," Thesis—Master of Science, University of Georgia, 2010.
European Extended Search Report for Application No. EP 15 17 2262, dated Dec. 2, 2015.
Carretero-Paulet et al., "Genome-wide classification and evolutionary analysis of the bHLH family of transcription factors in *Arabidopsis*, poplar, rice, moss, and algae," *Plant Physiol* 153:1398-1412, 2010.
Rhodes et al., "Hybrid Seed Production in Watermelon," *J of New Seeds* 1(3-4):69-88, 2000.
Yang et al., "Characterization of a New Male Sterile Mutant in Watermelon," *Cucurbit Genetics Coop Rpt* 24:52-58, 2001.
Zhang et al., "A genetic male-sterile (ms) watermelon from China," *Cucurbit Genetics Coop Rpt* 13:45, 1990.

* cited by examiner

*Primary Examiner* — Bratislav Stankovic
(74) *Attorney, Agent, or Firm* — Dentons US LLP; Alissa Eagle

(57) ABSTRACT

The present disclosure provides watermelon plants with a male sterile phenotype and their progeny. Such plants may comprise an introgressed genomic region associated with a male sterile phenotype. In certain aspects, compositions, including distinct polymorphic molecular markers and methods for producing, breeding, identifying, and selecting plants or germplasm with a male sterile phenotype are provided.

3 Claims, 3 Drawing Sheets

Specification includes a Sequence Listing.

FIG. 1

| Marker | NW0249314 | NW0249599 | NW0250496 | NW0249312 | NW0251153 | NW0248249 | NW0251340 | NW0248760 | NW0248489 | NW0249328 | NW0251464 | NW0248953 | NW0250301 |
|---|---|---|---|---|---|---|---|---|---|---|---|---|---|
| LG | 2 | 2 | 2 | 2 | 2 | 2 | 2 | 2 | 2 | 2 | 2 | 2 | 2 |
| Pos | 39.92 | 39.92 | 43.44 | 49.90 | 59.39 | 73.15 | 83.00 | 100.93 | 115.84 | 120.98 | 122.47 | 131.69 | 134.25 |
| WAS-39-5006S | TT | TT | TT | AA | AA | AG | AG | CC | AA | CC | AA | TT | GG |
| WAS-39-5007S | TT | TT | CT | AG | AC | AG | AG | CC | AA | CC | AA | TT | GG |
| WAS-4S-1129S | CT | CC | CT | AA | AA | GG | AG | AC | AA | CC | AA | AA | AG |
| WAS-4S-2058S | TT | TT | TT | AA | AA | AG | AG | AC | AA | CC | AA | AA | AA |
| WAS-4S-2068S | TT | TT | TT | AA | AA | AG | AG | AC | AA | CC | AA | AA | AA |
| WAS-4S-2078S | TT | TT | TT | AA | AA | AG | AG | AC | AA | CC | AA | AA | AG |
| WAS-4S-2088S | CC | CC | CC | GG | CC | AG | AG | AA | AA | CC | AA | AA | AA |
| WAS-4S-2098S | TT | TT | CC | GG | CC | AG | GG | CC | AA | GG | GG | TT | GG |
| WAS-4S-2128S | TT | TT | TT | AA | AA | AG | AG | AC | AA | CC | AA | AA | AA |
| WAS-4S-2138S | TT | CT | CT | AA | AA | AG | AG | AC | AA | CC | AA | AA | AG |
| WAS-4S-2158S | TT | TT | TT | AA | AA | AG | AG | AC | AA | CC | AA | AA | AG |
| WAS-4S-2288S | CT | CT | -- | AA | CC | AA | AG | AC | AA | CC | AA | AA | AA |
| WAS-4S-2378S | CC | CC | CC | AG | AC | AG | AG | AC | CC | CC | AA | AA | AG |
| WAS-4S-3108S | TT | TT | CC | GG | CC | AG | AG | AA | AA | CC | AA | AA | GG |
| WCS-146-2190S | TT | TT | TT | AA | AA | AA | GG | CC | AA | CC | AA | TT | AA |
| WCS-4S-1119S | CC | CC | CC | AG | AC | AG | AG | AC | CC | CC | AA | AA | AA |
| WCS-4S-2318S | CC | CC | CC | AG | AC | AG | AG | AC | CC | CC | AA | AA | AA |
| WCS-4S-2338S | TT | TT | CC | GG | CC | AA | AG | CC | AA | CC | AA | AA | GG |
| WCS-4S-2661S | CC | CC | CC | AG | AC | AG | AG | AC | AA | CC | AA | AA | AA |
| WCS-4S-2711S | CC | CC | CC | GG | CC | AA | AA | AA | CC | CC | AA | AA | GG |
| WCS-4S-2741S | CC | CC | CC | GG | CC | AA | AA | AA | CC | CC | AA | AA | GG |
| WDL-4S-1118S | TT | TT | CC | GG | CC | AA | AG | CC | AA | CC | AA | AA | AA |
| WDL-4S-1128S | CC | CC | CC | GG | AA | AG | AG | AC | AA | CG | AA | AA | AA |
| WDL-4S-116S | TT | TT | CC | GG | CC | AG | AG | CC | AA | CC | AA | AA | AA |
| WDL-4S-122S | TT | TT | CC | GG | AC | AG | AG | AC | AA | GG | GG | AT | AG |
| WJB-4S-102S | TT | TT | CC | AG | AC | AG | AG | CC | AC | GG | GG | TT | AG |
| WJB-4S-160S | TT | TT | TT | AA | AA | AG | AG | CC | AA | CC | AA | AA | AA |
| WJB-4S-3028S | TT | TT | CT | AG | AC | AG | AG | CC | AA | GG | GG | TT | GG |
| WML-146-4523S | CC | CC | CC | GG | AC | AA | GG | CC | AC | CC | AA | AA | AA |
| WML-146-4552S | TT | CT | CT | AG | AC | AA | GG | AA | AA | GG | AG | TT | AG |
| WML-146-9613S | CC | CC | CC | AA | AC | AA | GG | CC | CC | CC | AA | AA | AA |
| WML-4S-1019S | TT | TT | TT | AA | AC | AA | GG | CC | AA | CC | AA | AA | AA |
| WML-4S-121S | TT | TT | TT | AA | AA | AA | GG | CC | AA | CC | AA | AA | AA |
| WML-4S-1388S | CC | CC | CC | GG | CC | AG | GG | CC | AA | CC | AA | AA | AA |
| WML-4S-139S | TT | TT | CC | GG | CC | GG | GG | CC | AA | GG | GG | AA | AA |
| WML-4S-1448S | TT | TT | CC | GG | CC | AG | GG | CC | AA | GG | GG | AA | AA |
| WML-4S-144S | TT | TT | CC | GG | CC | AG | GG | CC | AA | GG | GG | AA | AA |
| WML-4S-1488S | TT | TT | CC | GG | CC | AG | AG | CC | AA | GG | GG | AA | AA |
| WML-4S-3038S | TT | TT | CT | AG | CC | AA | GG | CC | AA | CC | AA | AT | AA |
| WPC-4S-2358S | TT | TT | TT | AA | AC | AA | -- | CC | AA | CG | AG | AT | AG |
| WSB-37-1806S | TT | TT | CC | GG | CC | AA | AG | CC | AA | CC | AA | TT | AA |
| WSB-37-1808S | CC | CC | CC | GG | CC | AA | GG | CC | AA | CC | AA | AA | AA |
| WSB-4S-101S | TT | TT | CC | GG | CC | AA | GG | CC | AA | CC | AA | AA | AA |

FIG. 2

| QTL Position | 81.02 | 82.03 | 82.05 | 82.46 | 83.16 | 84.20 | |
|---|---|---|---|---|---|---|---|
| Marker | NCLAN009404570 | NCLAN009584571 | NCLAN009490296 | NCLAN009491448 | NCLAN009490864 | NCLAN009405170 | Ms-1 |
| | GT | Het | CG | CC | AA | AA | F |
| | GT | Het | CG | CC | AA | AA | F |
| | GT | Het | CG | CC | AA | AA | F |
| | GT | Het | CG | CG | AG | AA | F |
| | GT | Het | CG | CG | AG | AA | F |
| | GT | Het | CG | CG | AG | AA | F |
| | GT | Het | CG | CG | AG | AG | F |
| | GT | Het | CG | CG | AG | AG | F |
| | GT | Het | CG | CG | AG | AG | F |
| | GT | - | GG | CC | AA | AA | S |
| | GT | - | GG | CC | AA | AA | S |
| | GT | - | GG | CC | AA | AA | S |
| | GT | - | GG | CC | AA | AA | S |
| | TT | Het | CG | CG | AG | AG | F |
| | TT | Het | CG | CG | AG | AG | F |
| | TT | Het | CG | CG | AG | AG | F |
| | TT | - | GG | CC | AA | AA | S |
| | TT | - | GG | CC | AA | AA | S |
| | TT | - | GG | CC | AA | AG | S |
| | TT | - | GG | CC | AG | AG | S |
| | TT | - | GG | CC | AG | AG | S |
| | TT | - | GG | CC | AG | AG | S |
| | TT | - | GG | CG | AG | AG | S |
| | TT | - | GG | CG | AG | AG | S |
| | TT | - | GG | CG | AG | AG | S |

FIG. 3

```
                               SEQUENCE LISTING

<160> NUMBER OF SEQ ID NOS: 90

<210> SEQ ID NO 1
<211> LENGTH: 201
<212> TYPE: DNA
<213> ORGANISM: Citrullus lanatus
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 1
cctgcttctc aaatgttttt tttnaatatt tgtgggtgtc tgggcaagct ttttgtgca      60 ccttgactaa tctcacggga caacctgtct gacccttaaa natttgggtg tcaaggaaac   120
tcgtaggaaa ttaattccta ggtaggtggc caccatggat tgaaaccctt gatctcttag   180
tcatttattg agactataat g                                              201

<210> SEQ ID NO 2
<211> LENGTH: 17
<212> TYPE: DNA
<213> ORGANISM: Artificial sequence
<220> FEATURE:
<223> OTHER INFORMATION: probe

<400> SEQUENCE: 2
acacccaaat gtttaag                                                    17

<210> SEQ ID NO 3
<211> LENGTH: 17
<212> TYPE: DNA
<213> ORGANISM: Artificial sequence
<220> FEATURE:
<223> OTHER INFORMATION: probe

<400> SEQUENCE: 3
acacccaaat atttaag                                                    17

<210> SEQ ID NO 4
<211> LENGTH: 23
<212> TYPE: DNA
<213> ORGANISM: Artificial sequence
<220> FEATURE:
<223> OTHER INFORMATION: primer

<400> SEQUENCE: 4
tgactaatct cacgggacaa cct                                             23

<210> SEQ ID NO 5
<211> LENGTH: 24
<212> TYPE: DNA
<213> ORGANISM: Artificial sequence
<220> FEATURE:
<223> OTHER INFORMATION: primer

<400> SEQUENCE: 5
gtggccacct acctaggaat taat                                            24

<210> SEQ ID NO 6
```

```
<211> LENGTH: 201
<212> TYPE: DNA
<213> ORGANISM: Citrullus lanatus
<220> FEATURE:
<221> NAME/KEY: misc_feature
<222> LOCATION: (101)..(101)
<223> OTHER INFORMATION: n is a, c, g, or t

<400> SEQUENCE: 6
cataggacga aaagcacaac aaaaccattg gccaagacac tcaacagtag ccagttctcc    60
tttcgaaatg cttttgtgca acattaataa ggaaaatcag nagcatggag acagttttta   120
aggaaagggc aacaacagca agtgcaaaca aacagttaca atatttgcta acagcaacca   180
ccacaaacag atgcaggtaa a                                             201

<210> SEQ ID NO 7
<211> LENGTH: 201
<212> TYPE: DNA
<213> ORGANISM: Citrullus lanatus
<220> FEATURE:
<221> NAME/KEY: misc_feature
<222> LOCATION: (101)..(101)
<223> OTHER INFORMATION: n is a, c, g, or t

<400> SEQUENCE: 7
tctttggcgg aaaggcggtt gtagagagct tgcccagtga gagcttgctg gtaagtttgt    60
aagaggaaat ttcagcagca agtcaatctt cttatcataa ntcgtggata tgttgaattg   120
acaggttaaa catccaaggt tcagcaagga gagtttagaa gttaatgaaa ctatctacaa   180
acggcttctt gatctggctg c                                             201

<210> SEQ ID NO 8
<211> LENGTH: 19
<212> TYPE: DNA
<213> ORGANISM: Artificial sequence
<220> FEATURE:
<223> OTHER INFORMATION: probe

<400> SEQUENCE: 8
acatatccac gagttatga                                                 19

<210> SEQ ID NO 9
<211> LENGTH: 18
<212> TYPE: DNA
<213> ORGANISM: Artificial sequence
<220> FEATURE:
<223> OTHER INFORMATION: probe

<400> SEQUENCE: 9
catatccacg aattatga                                                  18

<210> SEQ ID NO 10
<211> LENGTH: 25
<212> TYPE: DNA
<213> ORGANISM: Artificial sequence
<220> FEATURE:
<223> OTHER INFORMATION: primer

<400> SEQUENCE: 10
ggaaatttca gcagcaagtc aatct                                          25

<210> SEQ ID NO 11
<211> LENGTH: 25
<212> TYPE: DNA
<213> ORGANISM: Artificial sequence
```

```
<220> FEATURE:
<223> OTHER INFORMATION: primer

<400> SEQUENCE: 11
tgaaccttgg atgtttaacc tgtca                                          25

<210> SEQ ID NO 12
<211> LENGTH: 201
<212> TYPE: DNA
<213> ORGANISM: Citrullus lanatus
<220> FEATURE:
<221> NAME/KEY: misc_feature
<222> LOCATION: (101)..(101)
<223> OTHER INFORMATION: n is a, c, g, or t

<400> SEQUENCE: 12
caaaggtgtt aactgtgatg gccaacttga gtttgtgaag tgacagacta aagtggaaga     60
tgaccaagaa aacttccgaa tcaaatcact gtagatttgg ncaggaaata gaaaccaacg    120
aaaaactata acacgaagaa cttctgtgtt agaaacagag acccacaaat tagaattgaa    180
acatgaagaa ctcatagact a                                              201

<210> SEQ ID NO 13
<211> LENGTH: 20
<212> TYPE: DNA
<213> ORGANISM: Artificial sequence
<220> FEATURE:
<223> OTHER INFORMATION: probe

<400> SEQUENCE: 13
ttctatttcc tgtccaaatc                                                20

<210> SEQ ID NO 14
<211> LENGTH: 16
<212> TYPE: DNA
<213> ORGANISM: Artificial sequence
<220> FEATURE:
<223> OTHER INFORMATION: probe

<400> SEQUENCE: 14
atttcctgcc caaatc                                                    16

<210> SEQ ID NO 15
<211> LENGTH: 27
<212> TYPE: DNA
<213> ORGANISM: Artificial sequence
<220> FEATURE:
<223> OTHER INFORMATION: primer

<400> SEQUENCE: 15
ccaagaaaac ttccgaatca aatcact                                        27

<210> SEQ ID NO 16
<211> LENGTH: 28
<212> TYPE: DNA
<213> ORGANISM: Artificial sequence
<220> FEATURE:
<223> OTHER INFORMATION: primer

<400> SEQUENCE: 16
gttcttcgtg ttatagtttt tcgttggt                                       28

<210> SEQ ID NO 17
<211> LENGTH: 120
<212> TYPE: DNA
```

```
<213> ORGANISM: Citrullus lanatus
<220> FEATURE:
<221> NAME/KEY: misc_feature
<222> LOCATION: (61)..(61)
<223> OTHER INFORMATION: n is a, c, g, or t

<400> SEQUENCE: 17
tctctcctcg gcacagaatt gcaaccgcaa gacctcgact atcaaggaga caactgtgga      60
ntctacagcc aagactgtat gcaggggact ttcaatccag cagatcttca ggtactttaa     120

<210> SEQ ID NO 18
<211> LENGTH: 17
<212> TYPE: DNA
<213> ORGANISM: Artificial sequence
<220> FEATURE:
<223> OTHER INFORMATION: probe

<400> SEQUENCE: 18
caactgtgga atctaca                                                    17

<210> SEQ ID NO 19
<211> LENGTH: 17
<212> TYPE: DNA
<213> ORGANISM: Artificial sequence
<220> FEATURE:
<223> OTHER INFORMATION: probe

<400> SEQUENCE: 19
caactgtgga ctctaca                                                    17

<210> SEQ ID NO 20
<211> LENGTH: 22
<212> TYPE: DNA
<213> ORGANISM: Artificial sequence
<220> FEATURE:
<223> OTHER INFORMATION: primer

<400> SEQUENCE: 20
gcaagacctc gactatcaag ga                                              22

<210> SEQ ID NO 21
<211> LENGTH: 23
<212> TYPE: DNA
<213> ORGANISM: Artificial sequence
<220> FEATURE:
<223> OTHER INFORMATION: primer

<400> SEQUENCE: 21
aaagtcccct gcatacagtc ttg                                             23

<210> SEQ ID NO 22
<211> LENGTH: 201
<212> TYPE: DNA
<213> ORGANISM: Citrullus lanatus

<400> SEQUENCE: 22
aaatgatgag ttccagaaat atagttcatc ttttgctgta acaagcttta ctgtgcatct      60
tagagataag atcaatgtgg tgtcgaatat cgagagaaca aatcttaact ccaaagcttg     120
tatgcatgaa aacatatcga gatttactta agagaaaact accagctttt tccaactctc     180
tttatttcat gattccatct t                                               201

<210> SEQ ID NO 23
<211> LENGTH: 119
```

```
<212> TYPE: DNA
<213> ORGANISM: Citrullus lanatus
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t

<400> SEQUENCE: 23
ttagacaaac ctttgctagc tatggcaatt tatgagtgta tcctatggaa gttgtttctt     60
ntgtttaaaa aanctgtttg agttaatttc aattgtgaaa atctttagtg gatgaaatt    119

<210> SEQ ID NO 24
<211> LENGTH: 23
<212> TYPE: DNA
<213> ORGANISM: Artificial sequence
<220> FEATURE:
<223> OTHER INFORMATION: probe

<400> SEQUENCE: 24
atggaagttg tttcttatgt tta                                            23

<210> SEQ ID NO 25
<211> LENGTH: 22
<212> TYPE: DNA
<213> ORGANISM: Artificial sequence
<220> FEATURE:
<223> OTHER INFORMATION: probe

<400> SEQUENCE: 25
tggaagttgt ttcttttgtt ta                                             22

<210> SEQ ID NO 26
<211> LENGTH: 26
<212> TYPE: DNA
<213> ORGANISM: Artificial sequence
<220> FEATURE:
<223> OTHER INFORMATION: primer

<400> SEQUENCE: 26
tgctagctat ggcaatttat gagtgt                                         26

<210> SEQ ID NO 27
<211> LENGTH: 31
<212> TYPE: DNA
<213> ORGANISM: Artificial sequence
<220> FEATURE:
<223> OTHER INFORMATION: primer

<400> SEQUENCE: 27
aatttcatcc actaaagatt ttcacaattg a                                   31

<210> SEQ ID NO 28
<211> LENGTH: 191
<212> TYPE: DNA
<213> ORGANISM: Citrullus lanatus

<400> SEQUENCE: 28
ctatcgtcac ttattcggct tgtgagaacc gttttagat gatgagaggg aaaaaggaag     60
aaaaattctt cagaaaccct cctttaaaat tgggagaatt tcttagaga gaatatctgc    120 aaaatggttg tatcagctaa ggatgatgct tacacccttt tatattttgt gcattttaa    180
```
ttcaaatcaa g                                                          191

<210> SEQ ID NO 29
<211> LENGTH: 20
<212> TYPE: DNA
<213> ORGANISM: Artificial sequence
<220> FEATURE:
<223> OTHER INFORMATION: probe

<400> SEQUENCE: 29
attttcttag agagaatatc                                                  20

<210> SEQ ID NO 30
<211> LENGTH: 21
<212> TYPE: DNA
<213> ORGANISM: Artificial sequence
<220> FEATURE:
<223> OTHER INFORMATION: probe

<400> SEQUENCE: 30
aattttctta gagataatat c                                                21

<210> SEQ ID NO 31
<211> LENGTH: 27
<212> TYPE: DNA
<213> ORGANISM: Artificial sequence
<220> FEATURE:
<223> OTHER INFORMATION: primer

<400> SEQUENCE: 31
ttcagaaacc ctcctttaaa attggga                                          27

<210> SEQ ID NO 32
<211> LENGTH: 26
<212> TYPE: DNA
<213> ORGANISM: Artificial sequence
<220> FEATURE:
<223> OTHER INFORMATION: primer

<400> SEQUENCE: 32
tccttagctg atacaaccat tttgca                                           26

<210> SEQ ID NO 33
<211> LENGTH: 240
<212> TYPE: DNA
<213> ORGANISM: Citrullus lanatus

<400> SEQUENCE: 33
atttgtgctt tcaacatccc acgcgccgcc cccttctaat tcctccgccg tcctgtgcct       60
cttgctcctc tctctgctgc atctcttctt ctccaccagc agtttcagtt ccttcacttc      120
tcttaaaagc tcttggatgt aatttatggc gtctcccaca actgatgccc tatcattctg      180
gtttaataac aaaatcacag gaaagactga ttaaaattgc tcacacccag atactgaatt      240

<210> SEQ ID NO 34
<211> LENGTH: 18
<212> TYPE: DNA
<213> ORGANISM: Artificial sequence
<220> FEATURE:
<223> OTHER INFORMATION: probe

<400> SEQUENCE: 34
tctccaccag cagtttca                                                    18

```
<210> SEQ ID NO 35
<211> LENGTH: 19
<212> TYPE: DNA
<213> ORGANISM: Artificial sequence
<220> FEATURE:
<223> OTHER INFORMATION: probe

<400> SEQUENCE: 35
ttctccacca gcacttcac                                                    19

<210> SEQ ID NO 36
<211> LENGTH: 18
<212> TYPE: DNA
<213> ORGANISM: Artificial sequence
<220> FEATURE:
<223> OTHER INFORMATION: primer

<400> SEQUENCE: 36
ctctctctgc tgcatctc                                                     18

<210> SEQ ID NO 37
<211> LENGTH: 20
<212> TYPE: DNA
<213> ORGANISM: Artificial sequence
<220> FEATURE:
<223> OTHER INFORMATION: primer

<400> SEQUENCE: 37
cagtctttcc tgtgattttg                                                   20

<210> SEQ ID NO 38
<211> LENGTH: 196
<212> TYPE: DNA
<213> ORGANISM: Citrullus lanatus
<220> FEATURE:
<221> NAME/KEY: misc_feature
<222> LOCATION: (91)..(91)
<223> OTHER INFORMATION: n is a, c, g, or t

<400> SEQUENCE: 38
aaggtctcca agaaagcctc ccatgggtga ggtatggtga ttggagaagg agatggaaga       60
gttgttgggg catctggcag gggccggcat ntttaagaag ttcaagaggt ccggagcttg      120
agtataggca gtgggcatgg cggaatctga aaactgctgc tggtgcggat gatgatggtg      180
atcttgagat tgaatc                                                      196

<210> SEQ ID NO 39
<211> LENGTH: 16
<212> TYPE: DNA
<213> ORGANISM: Artificial sequence
<220> FEATURE:
<223> OTHER INFORMATION: probe

<400> SEQUENCE: 39
tcaagctccg gacctc                                                       16

<210> SEQ ID NO 40
<211> LENGTH: 15
<212> TYPE: DNA
<213> ORGANISM: Artificial sequence
<220> FEATURE:
<223> OTHER INFORMATION: probe

<400> SEQUENCE: 40
caagctcccg acctc                                                        15
```

<210> SEQ ID NO 41
<211> LENGTH: 25
<212> TYPE: DNA
<213> ORGANISM: Artificial sequence
<220> FEATURE:
<223> OTHER INFORMATION: primer

<400> SEQUENCE: 41
ggagaaggag atggaagagt tgttg                                    25

<210> SEQ ID NO 42
<211> LENGTH: 20
<212> TYPE: DNA
<213> ORGANISM: Artificial sequence
<220> FEATURE:
<223> OTHER INFORMATION: primer

<400> SEQUENCE: 42
gccatgccca ctgcctatac                                          20

<210> SEQ ID NO 43
<211> LENGTH: 204
<212> TYPE: DNA
<213> ORGANISM: Citrullus lanatus

<400> SEQUENCE: 43
aaagattgag attattgtca tgaaaattgg gatgggtttc ttgggcagcg gcggcaatga    60
gtggcggagg aaaggaaggc aaagcaacag aaatatgggg gacagtatga ggaaaggcat   120
tttgtgaagg atctggtaga gtggaatcgg gatcagaaca cccagtttgt tcatacatat   180
tttggtaaga aaagtgtgca gctt                                         204

<210> SEQ ID NO 44
<211> LENGTH: 17
<212> TYPE: DNA
<213> ORGANISM: Artificial sequence
<220> FEATURE:
<223> OTHER INFORMATION: probe

<400> SEQUENCE: 44
tcctcatact gtccccc                                             17

<210> SEQ ID NO 45
<211> LENGTH: 16
<212> TYPE: DNA
<213> ORGANISM: Artificial sequence
<220> FEATURE:
<223> OTHER INFORMATION: probe

<400> SEQUENCE: 45
cctcatacta tccccc                                              16

<210> SEQ ID NO 46
<211> LENGTH: 25
<212> TYPE: DNA
<213> ORGANISM: Artificial sequence
<220> FEATURE:
<223> OTHER INFORMATION: primer

<400> SEQUENCE: 46
gaaaggaagg caaagcaaca gaaat                                    25

<210> SEQ ID NO 47
<211> LENGTH: 25

```
<212> TYPE: DNA
<213> ORGANISM: Artificial sequence
<220> FEATURE:
<223> OTHER INFORMATION: primer

<400> SEQUENCE: 47
ccactctacc agatccttca caaaa                                           25

<210> SEQ ID NO 48
<211> LENGTH: 149
<212> TYPE: DNA
<213> ORGANISM: Citrullus lanatus

<400> SEQUENCE: 48
gttgcaccac cattattatt attattagcc tctgtcttgt tgttagatga gttgttatta    60 ttagaccccca aggcattgag ttgaactttg gtaggtttca agcaatgatg caaataaacc  120
aaaagccaaa agatccaggg agttgaaac                                      149

<210> SEQ ID NO 49
<211> LENGTH: 18
<212> TYPE: DNA
<213> ORGANISM: Artificial sequence
<220> FEATURE:
<223> OTHER INFORMATION: probe

<400> SEQUENCE: 49
attagacccc aaggcatt                                                   18

<210> SEQ ID NO 50
<211> LENGTH: 17
<212> TYPE: DNA
<213> ORGANISM: Artificial sequence
<220> FEATURE:
<223> OTHER INFORMATION: probe

<400> SEQUENCE: 50
ttagagccca aggcatt                                                    17

<210> SEQ ID NO 51
<211> LENGTH: 25
<212> TYPE: DNA
<213> ORGANISM: Artificial sequence
<220> FEATURE:
<223> OTHER INFORMATION: primer

<400> SEQUENCE: 51
gcctctgtct tgttgttaga tgagt                                           25

<210> SEQ ID NO 52
<211> LENGTH: 25
<212> TYPE: DNA
<213> ORGANISM: Artificial sequence
<220> FEATURE:
<223> OTHER INFORMATION: primer

<400> SEQUENCE: 52
gcatcattgc ttgaaaccta ccaaa                                           25

<210> SEQ ID NO 53
<211> LENGTH: 120
<212> TYPE: DNA
<213> ORGANISM: Citrullus lanatus

<400> SEQUENCE: 53
```

```
agcggatgac tacatctgct aatgagaaga agtgtgaggc ggaacatgct atgggagatt    60
aggtttactt gaaactgcga ccatgtcgga atacgtcgtt gtttccacac acgcatccaa   120
```

<210> SEQ ID NO 54
<211> LENGTH: 157
<212> TYPE: DNA
<213> ORGANISM: Citrullus lanatus

<400> SEQUENCE: 54

```
attgtgttga gaaaagccaa gaaggaaaat gtggtatact tcatccgaac tcacattatt    60
tatcagtaca acattcctca ttgaattgtg atagataatg aagacagtt ttccaatagt    120 ttgaagaata aattatgtga gaaattcaag tcaagca                             157
```

<210> SEQ ID NO 55
<211> LENGTH: 20
<212> TYPE: DNA
<213> ORGANISM: Artificial sequence
<220> FEATURE:
<223> OTHER INFORMATION: probe

<400> SEQUENCE: 55

```
ttgaattgtg atagataatg                                                 20
```

<210> SEQ ID NO 56
<211> LENGTH: 19
<212> TYPE: DNA
<213> ORGANISM: Artificial sequence
<220> FEATURE:
<223> OTHER INFORMATION: probe

<400> SEQUENCE: 56

```
tgaattgtga tggataatg                                                  19
```

<210> SEQ ID NO 57
<211> LENGTH: 31
<212> TYPE: DNA
<213> ORGANISM: Artificial sequence
<220> FEATURE:
<223> OTHER INFORMATION: primer

<400> SEQUENCE: 57

```
gtggtatact tcatccgaac tcacattatt t                                    31
```

<210> SEQ ID NO 58
<211> LENGTH: 37
<212> TYPE: DNA
<213> ORGANISM: Artificial sequence
<220> FEATURE:
<223> OTHER INFORMATION: primer

<400> SEQUENCE: 58

```
cacataattt attcttcaaa ctattggaaa actgtct                              37
```

<210> SEQ ID NO 59
<211> LENGTH: 220
<212> TYPE: DNA
<213> ORGANISM: Citrullus lanatus

<400> SEQUENCE: 59

```
atcagtatat aagccaggtg catcatttat caagtatatc aaatttatca acaatatata    60
ataaatattc aagtatatca gtcaagtgca tcgttatcaa gtatattagt caaatatatc   120
aaatgtatat gaagggtatc aaatcagtgt atcaagtgta tttatacaca gtagtgtatc   180
```

```
aagggtatca agtgtgtata gtgtatcaag tgtatcaagt                          220
```

<210> SEQ ID NO 60
<211> LENGTH: 23
<212> TYPE: DNA
<213> ORGANISM: Artificial sequence
<220> FEATURE:
<223> OTHER INFORMATION: probe

<400> SEQUENCE: 60

```
caagtatatt agtcaaatat atc                                            23
```

<210> SEQ ID NO 61
<211> LENGTH: 23
<212> TYPE: DNA
<213> ORGANISM: Artificial sequence
<220> FEATURE:
<223> OTHER INFORMATION: probe

<400> SEQUENCE: 61

```
caagtatatt agtcaagtat atc                                            23
```

<210> SEQ ID NO 62
<211> LENGTH: 28
<212> TYPE: DNA
<213> ORGANISM: Artificial sequence
<220> FEATURE:
<223> OTHER INFORMATION: primer

<400> SEQUENCE: 62

```
ttcaagtata tcagtcaagt gcatcgtt                                       28
```

<210> SEQ ID NO 63
<211> LENGTH: 29
<212> TYPE: DNA
<213> ORGANISM: Artificial sequence
<220> FEATURE:
<223> OTHER INFORMATION: primer

<400> SEQUENCE: 63

```
cacttgatac actgatttga taccttca                                       29
```

<210> SEQ ID NO 64
<211> LENGTH: 201
<212> TYPE: DNA
<213> ORGANISM: Citrullus lanatus

<400> SEQUENCE: 64

```
agaaacgtgt aatagtcgcc acagcagaat aagcattatt taaatcgtgc tgtttgcaaa    60
gaaatggagt cttactactg ttcatccatt caatgattgc aaactaatca agaaacaaa    120
acaaatcaac atcgaagcaa tttacaattc caagtaaaga tttgatttat ggtcggaaac   180
agaatcaaaa tcaatattac c                                             201
```

<210> SEQ ID NO 65
<211> LENGTH: 218
<212> TYPE: DNA
<213> ORGANISM: Citrullus lanatus

<400> SEQUENCE: 65

```
ttaacttgtt accaatgtgt tgaaaaattt aaaatattg aaataaatgg acattctttt    60
ttcgcgtctg agcaggtttg tgtcatgtca acactgacac ttagcaacat aaatagtgtg  120
```

```
ccttctagct tgaaatgtaa ttgcttatat gagttatttt cttgaaggat tatagatgga      180
gaaacaagaa ttggcatatt tgcaactcga gacataca                             218
```

<210> SEQ ID NO 66
<211> LENGTH: 20
<212> TYPE: DNA
<213> ORGANISM: Artificial sequence
<220> FEATURE:
<223> OTHER INFORMATION: probe

<400> SEQUENCE: 66

```
ttgtgtcatg tcaacactga                                                  20
```

<210> SEQ ID NO 67
<211> LENGTH: 17
<212> TYPE: DNA
<213> ORGANISM: Artificial sequence
<220> FEATURE:
<223> OTHER INFORMATION: probe

<400> SEQUENCE: 67

```
tgtcatgtcg acactga                                                     17
```

<210> SEQ ID NO 68
<211> LENGTH: 19
<212> TYPE: DNA
<213> ORGANISM: Artificial sequence
<220> FEATURE:
<223> OTHER INFORMATION: primer

<400> SEQUENCE: 68

```
ttttcgcgtc tgagcaggt                                                   19
```

<210> SEQ ID NO 69
<211> LENGTH: 24
<212> TYPE: DNA
<213> ORGANISM: Artificial sequence
<220> FEATURE:
<223> OTHER INFORMATION: primer

<400> SEQUENCE: 69

```
acatttcaag ctagaaggca cact                                             24
```

<210> SEQ ID NO 70
<211> LENGTH: 122
<212> TYPE: DNA
<213> ORGANISM: Citrullus lanatus

<400> SEQUENCE: 70

```
ctctccatgg ctgcttggct tctccatagc cccatattaa ggtctcaaag gtttcaaat       60 tggggacac atccatttca cacatatgct caaaaccct acatgccttc tccatttac        120 cc                                                                    122
```

<210> SEQ ID NO 71
<211> LENGTH: 128
<212> TYPE: DNA
<213> ORGANISM: Citrullus lanatus

<400> SEQUENCE: 71

```
gcttggctta tgacactaac aggtgagctc aaaacagctt tgggtcagc ttcatcgaga       60 gccttatccg aagcaaaatt gggattctct tcaagccaac tcgcaatgag ccgtttgagc     120
acataatt                                                              128
```

```
<210> SEQ ID NO 72
<211> LENGTH: 120
<212> TYPE: DNA
<213> ORGANISM: Citrullus lanatus
<220> FEATURE:
<221> NAME/KEY: misc_feature
<222> LOCATION: (17)..(17)
<223> OTHER INFORMATION: n is a, c, g, or t

<400> SEQUENCE: 72
gacaactgca agagaanttt ttcaacatga aacattcttc agcaaggaat gttatcgagc    60
aagcgtttgg gttgctaaag cagcagtggg ctattcttag tgaaacataa ttctatccaa   120

<210> SEQ ID NO 73
<211> LENGTH: 201
<212> TYPE: DNA
<213> ORGANISM: Citrullus lanatus

<400> SEQUENCE: 73
aaagtgtcgt ctatcaaatc tattaatgga gcttgactgt ttgaaagtta ttcgtttact    60
gaatgatgag gcgattggca tatcaaaagt ctcctttatt agacgaggct aagagttgtg   120
gatatgatct ggaagttgtc tctttctctc atattcgtta taatcagaat gcgttggtgc   180
acttttttgc acaaaaggct t                                             201

<210> SEQ ID NO 74
<211> LENGTH: 17
<212> TYPE: DNA
<213> ORGANISM: Artificial sequence
<220> FEATURE:
<223> OTHER INFORMATION: probe

<400> SEQUENCE: 74
tagcctcgtc taataaa                                                   17

<210> SEQ ID NO 75
<211> LENGTH: 14
<212> TYPE: DNA
<213> ORGANISM: Artificial sequence
<220> FEATURE:
<223> OTHER INFORMATION: probe

<400> SEQUENCE: 75
cctcgtcaaa taaa                                                      14

<210> SEQ ID NO 76
<211> LENGTH: 24
<212> TYPE: DNA
<213> ORGANISM: Artificial sequence
<220> FEATURE:
<223> OTHER INFORMATION: primer

<400> SEQUENCE: 76
gaggcgattg gcatatcaaa agtc                                           24

<210> SEQ ID NO 77
<211> LENGTH: 27
<212> TYPE: DNA
<213> ORGANISM: Artificial sequence
<220> FEATURE:
<223> OTHER INFORMATION: primer

<400> SEQUENCE: 77
```
agacaacttc cagatcatat ccacaac                                          27

<210> SEQ ID NO 78
<211> LENGTH: 195
<212> TYPE: DNA
<213> ORGANISM: Citrullus lanatus
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t

<400> SEQUENCE: 78
ggcttgtgat cttaagcttt ccaccaacaa aanggccttt ggtggaacta agctcgacaa      60
caatgagcat caacctaccg agcgagaagg cactattgcg attagcaaca tggaaaagta    120
gtcctgatct tcgttctcgt gtagactatg tcttaggact tggtctttgt tttnattgct    180
tttgttgtgt tagct                                                     195

<210> SEQ ID NO 79
<211> LENGTH: 17
<212> TYPE: DNA
<213> ORGANISM: Artificial sequence
<220> FEATURE:
<223> OTHER INFORMATION: probe

<400> SEQUENCE: 79
cactattgcg attagca                                                    17

<210> SEQ ID NO 80
<211> LENGTH: 17
<212> TYPE: DNA
<213> ORGANISM: Artificial sequence
<220> FEATURE:
<223> OTHER INFORMATION: probe

<400> SEQUENCE: 80
cactattgcg gttagca                                                    17

<210> SEQ ID NO 81
<211> LENGTH: 22
<212> TYPE: DNA
<213> ORGANISM: Artificial sequence
<220> FEATURE:
<223> OTHER INFORMATION: primer

<400> SEQUENCE: 81
catcaaccta ccgagcgaga ag                                              22

<210> SEQ ID NO 82
<211> LENGTH: 25
<212> TYPE: DNA
<213> ORGANISM: Artificial sequence
<220> FEATURE:
<223> OTHER INFORMATION: primer

<400> SEQUENCE: 82
cgagaacgaa gatcaggact acttt                                           25

<210> SEQ ID NO 83
<211> LENGTH: 10
<212> TYPE: DNA
<213> ORGANISM: Citrullus lanatus

<400> SEQUENCE: 83
gtttcagttc                                                          10

<210> SEQ ID NO 84
<211> LENGTH: 70
<212> TYPE: DNA
<213> ORGANISM: Citrullus lanatus

<400> SEQUENCE: 84
ttgctcctct ctctgctgca tctcttcttc tccaccagca gtttcagttc cttcacttct    60
cttaaaagct                                                          70

<210> SEQ ID NO 85
<211> LENGTH: 60
<212> TYPE: DNA
<213> ORGANISM: Citrullus lanatus

<400> SEQUENCE: 85
ttgctcctct ctctgctgca tctcttcttc tccaccagca cttcacttct cttaaaagct    60

<210> SEQ ID NO 86
<211> LENGTH: 70
<212> TYPE: DNA
<213> ORGANISM: Citrullus lanatus

<400> SEQUENCE: 86
ttgctcctct ctctgctgca tctcttcttc tccaccagca gtttcagttc cttcacttct    60
cttaaaagct                                                          70

<210> SEQ ID NO 87
<211> LENGTH: 60
<212> TYPE: DNA
<213> ORGANISM: Citrullus lanatus

<400> SEQUENCE: 87
ttgctcctct ctctgctgca tctcttcttc tccaccagca cttcacttct cttaaaagct    60

<210> SEQ ID NO 88
<211> LENGTH: 70
<212> TYPE: DNA
<213> ORGANISM: Citrullus lanatus

<400> SEQUENCE: 88
ttgctcctct ctctgctgca tctcttcttc tccaccagca gtttcagttc cttcacttct    60
cttaaaagct                                                          70

<210> SEQ ID NO 89
<211> LENGTH: 70
<212> TYPE: DNA
<213> ORGANISM: Citrullus lanatus

<400> SEQUENCE: 89
ttgctcctct ctctgctgca tctcttcttc tccaccagca gtttcagttc cttcacttct    60
cttaaaagct                                                          70

<210> SEQ ID NO 90
<211> LENGTH: 70
<212> TYPE: DNA
<213> ORGANISM: Citrullus lanatus

```
<400> SEQUENCE: 90
ttgctcctct ctctgctgca tctcttcttc tccaccagca gtttcagttc cttcacttct      60
cttaaaagct                                                             70
```

METHODS AND ASSAYS FOR MALE STERILE WATERMELON

REFERENCE TO RELATED APPLICATIONS

This application claims the benefit of United States Provisional Application No. 62/018,413 filed Jun. 27, 2014, which is incorporated herein by reference in its entirety.

FIELD OF THE INVENTION

The present invention relates to the field of plant breeding and more specifically to methods and compositions for producing watermelon plants with male sterile phenotypes.

INCORPORATION OF SEQUENCE LISTING

The sequence listing that is contained in the file named "SEMB:016US-revised-ST25.txt", which is 20 kilobytes as measured in the Microsoft Windows operating system and was created on Dec. 31, 2015, is filed electronically herewith and incorporated herein by reference.

BACKGROUND OF THE INVENTION

Advances in molecular genetics have made it possible to select plants based on genetic markers linked to traits of interest, a process called marker-assisted selection (MAS). While breeding efforts to date have provided a number of useful watermelon lines and varieties with beneficial traits, there remains a need in the art for selection of varieties with further improved traits and methods for their production. In many cases, such efforts have been hampered by difficulties in identifying and using alleles conferring beneficial traits. These efforts can be confounded by the lack of definitive phenotypic assays, and other issues such as epistasis and polygenic or quantitative inheritance. In the absence of molecular tools such as MAS, it may not be practical to attempt to produce certain new genotypes of crop plants due to such challenges.

SUMMARY OF THE INVENTION

In one aspect, the present invention provides methods of determining the genotype associated with a male sterile phenotype of a watermelon plant or part thereof, comprising the steps of: obtaining a sample of material from said plant or part thereof; and detecting in said sample at least a first polymorphism in or genetically linked to a locus that confers said male sterile phenotype comprising loci NW0249314 (SEQ ID NO: 1) and NW0250301 (SEQ ID NO: 78) or within 15 cM thereof. The invention further provides watermelon plants or parts thereof obtained by said methods.

In another aspect, the invention provides methods of identifying a watermelon plant comprising a genotype associated with a male sterile phenotype, comprising the step of detecting in said plant at least a first polymorphism in or genetically linked to a locus that confers said male sterile phenotype comprising loci NW0249314 (SEQ ID NO: 1) and NW0250301 (SEQ ID NO: 78) on LG2. In some embodiments, said methods further comprise the step of selecting said watermelon plant from a population of watermelon plants based on the presence of said polymorphism. In certain embodiments, the polymorphism is selected from the group consisting of: NW0249314 (SEQ ID NO: 1), NW0249599 (SEQ ID NO: 6), NW0250496 (SEQ ID NO: 7), NW0249312 (SEQ ID NO: 12), NW0251153 (SEQ ID NO: 17), NW0248249 (SEQ ID NO: 22), NW0251130 (SEQ ID NO: 23), NCLAN009404570 (SEQ ID NO: 28), NCLAN009584571 (SEQ ID NO: 33), NCLAN009490296 (SEQ ID NO: 38), NCLAN009490491 (SEQ ID NO: 43), NCLAN009491448 (SEQ ID NO: 48), NW0251340 (SEQ ID NO: 53), NCLAN009490864 (SEQ ID NO: 54), NCLAN009405170 (SEQ ID NO: 59), NW0248760 (SEQ ID NO: 64), NCLAN009104771 (SEQ ID NO: 65), NW0248489 (SEQ ID NO: 70), NW0249128 (SEQ ID NO: 71), NW0251464 (SEQ ID NO: 72), NW0248953 (SEQ ID NO: 73), and NW0250301 (SEQ ID NO: 78). In further embodiments, the polymorphism is further defined as located in a genomic region flanked by: loci NCLAN009404570 (SEQ ID NO: 28) and NCLAN009405170 (SEQ ID NO: 59) on LG2. In yet further embodiments, the polymorphism is NCLAN009584571 (SEQ ID NO: 33). The invention further provides watermelon plants or parts thereof obtained by said methods.

In one aspect, the invention provides methods for producing a watermelon plant that comprises in its genome at least one locus associated with a male sterile phenotype, the method comprising: (i) crossing a first watermelon plant and a second watermelon plant at least one of which comprises a locus associated with a male sterile phenotype defined by: loci NW0249314 (SEQ ID NO: 1) and NW0250301 (SEQ ID NO: 78) on LG2, or within 15 cM thereof; (ii) detecting at least a first polymorphism in or genetically linked to said locus associated with a male sterile phenotype; and (iii) selecting a watermelon plant based on the presence of said polymorphism. In certain embodiments, said methods further comprise the step of (iv) crossing the watermelon plant of step (iii) with itself or another watermelon plant to produce a further generation. In further embodiments, said methods further comprise the step of: (v) selecting a watermelon plant from the further generation based on the presence of said polymorphism. In yet further embodiments, steps (iii)-(v) of said methods are repeated from about 3 times to about 10 times. In certain embodiments, said polymorphism is selected from the group consisting of: NW0249314 (SEQ ID NO: 1), NW0249599 (SEQ ID NO: 6), NW0250496 (SEQ ID NO: 7), NW0249312 (SEQ ID NO: 12), NW0251153 (SEQ ID NO: 17), NW0248249 (SEQ ID NO: 22), NW0251130 (SEQ ID NO: 23), NCLAN009404570 (SEQ ID NO: 28), NCLAN009584571 (SEQ ID NO: 33), NCLAN009490296 (SEQ ID NO: 38), NCLAN009490491 (SEQ ID NO: 43), NCLAN009491448 (SEQ ID NO: 48), NW0251340 (SEQ ID NO: 53), NCLAN009490864 (SEQ ID NO: 54), NCLAN009405170 (SEQ ID NO: 59), NW0248760 (SEQ ID NO: 64), NCLAN009104771 (SEQ ID NO: 65), NW0248489 (SEQ ID NO: 70), NW0249128 (SEQ ID NO: 71), NW0251464 (SEQ ID NO: 72), NW0248953 (SEQ ID NO: 73), and NW0250301 (SEQ ID NO: 78). In further embodiments, said polymorphism is located in or genetically linked to a genomic region defined by: loci NCLAN009404570 (SEQ ID NO: 28) and NCLAN009405170 (SEQ ID NO: 59) on LG2; or within 15 cM thereof. In yet further embodiments, said polymorphism is NCLAN009584571 (SEQ ID NO: 33). The invention further provides watermelon plants or parts thereof obtained by said methods.

In a further aspect, the invention provides methods of introgressing an allele into a watermelon plant, the method comprising: (i) genotyping at least one watermelon plant in a population with respect to at least one polymorphism located in or genetically linked to a genomic region defined by: loci NW0249314 (SEQ ID NO: 1) and NW0250301 (SEQ ID NO: 78) on LG2, or within 15 cM thereof; and (ii)

selecting from the population at least one watermelon plant comprising at least one allele associated with a male sterile phenotype. In certain embodiments, said polymorphism is selected from the group consisting of: NW0249314 (SEQ ID NO: 1), NW0249599 (SEQ ID NO: 6), NW0250496 (SEQ ID NO: 7), NW0249312 (SEQ ID NO: 12), NW0251153 (SEQ ID NO: 17), NW0248249 (SEQ ID NO: 22), NW0251130 (SEQ ID NO: 23), NCLAN009404570 (SEQ ID NO: 28), NCLAN009584571 (SEQ ID NO: 33), NCLAN009490296 (SEQ ID NO: 38), NCLAN009490491 (SEQ ID NO: 43), NCLAN009491448 (SEQ ID NO: 48), NW0251340 (SEQ ID NO: 53), NCLAN009490864 (SEQ ID NO: 54), NCLAN009405170 (SEQ ID NO: 59), NW0248760 (SEQ ID NO: 64), NCLAN009104771 (SEQ ID NO: 65), NW0248489 (SEQ ID NO: 70), NW0249128 (SEQ ID NO: 71), NW0251464 (SEQ ID NO: 72), NW0248953 (SEQ ID NO: 73), and NW0250301 (SEQ ID NO: 78). In further embodiments, said polymorphism is located in a genomic region flanked by: loci NCLAN009404570 (SEQ ID NO: 28) and NCLAN009405170 (SEQ ID NO: 59) on LG2; or within 15 cM thereof. In yet further embodiments, the polymorphism is NCLAN009584571 (SEQ ID NO: 33). The invention further provides watermelon plants or parts thereof obtained by said methods.

In yet another aspect, the invention provides a probe or primer sequence for detecting the presence of an allele in a watermelon plant, said marker comprising a sequence selected from the group consisting of: NW0249314 (SEQ ID NO: 1), NW0249599 (SEQ ID NO: 6), NW0250496 (SEQ ID NO: 7), NW0249312 (SEQ ID NO: 12), NW0251153 (SEQ ID NO: 17), NW0248249 (SEQ ID NO: 22), NW0251130 (SEQ ID NO: 23), NCLAN009404570 (SEQ ID NO: 28), NCLAN009584571 (SEQ ID NO: 33), NCLAN009490296 (SEQ ID NO: 38), NCLAN009490491 (SEQ ID NO: 43), NCLAN009491448 (SEQ ID NO: 48), NW0251340 (SEQ ID NO: 53), NCLAN009490864 (SEQ ID NO: 54), NCLAN009405170 (SEQ ID NO: 59), NW0248760 (SEQ ID NO: 64), NCLAN009104771 (SEQ ID NO: 65), NW0248489 (SEQ ID NO: 70), NW0249128 (SEQ ID NO: 71), NW0251464 (SEQ ID NO: 72), NW0248953 (SEQ ID NO: 73), and NW0250301 (SEQ ID NO: 78).

BRIEF DESCRIPTION OF THE DRAWINGS

FIG. 1: Shows data for markers in the interval of NW0249314 (SEQ ID NO: 1)/NW0249599 (SEQ ID NO: 6) and NW0250301 (SEQ ID NO: 78). Germplasm shown represents diverse watermelon breeding lines carrying the ms-1 introgression for which male sterility is maintained. A region of heterozygosity was identified for some of these lines near the SNP markers NW0248249 (SEQ ID NO: 22), NW0251340 (SEQ ID NO: 53), and NW0248760 (SEQ ID NO: 64). The markers shaded in gray are the indicated region of ms-1 gene as estimated from inference of genetic distance on the consensus map. The marker alleles shaded in gray are the indicated heterozygotic condition of the two marker alleles at that marker locus.

FIG. 2: Shows genotype and phenotype data for representative lines from fine mapping populations. Gray shading denotes fertile, no shading denotes sterile.

FIG. 3: Shows a sequence alignment for two sterile families (WAS-45-2158S and WML-45-144S) showing the 10 bp deletion in the sterile lines assayed by marker NCLAN009584571 (SEQ ID NO: 33). The sequences labeled 2158S-Fertile (SEQ ID NO:84), 2158S-Sterile (SEQ ID NO:85), 114S-Fertile (SEQ ID NO:86), and 114S-Sterile (SEQ ID NO:87) are sequences surrounding marker NCLAN009584571 (SEQ ID NO: 33). A reference sequence (SEQ ID NO:88), consensus sequence (SEQ ID NO:89), and sequence logo (SEQ ID NO:90) are also shown.

DETAILED DESCRIPTION OF THE INVENTION

Hybrid watermelon varieties typically exhibit higher yield, higher quality, and more uniform fruit size than open pollinated varieties. Commercial watermelon hybrid varieties include both diploids and triploids. A diploid hybrid is made by crossing two inbred diploid parent lines. A triploid hybrid is made by crossing a tetraploid female parent line with a diploid male parent line. Controlled pollination is essential to hybrid seed production. The production of hybrid seed by controlled pollination requires that both male and female flower buds are protected and that female flowers are hand-pollinated. Controlled pollination is labor-intensive and the cost of hybrid seed can be 10-100 times that of open-pollinated seed. The development and use of male sterile watermelon varieties can greatly reduce the cost of hybrid seed production as the pollen production in the female parent line is eliminated. The use of a male sterile line eliminates the need for controlled pollination.

Male sterility is the failure of plants to produce functional anthers, pollen, or male gametes. Male sterility facilitates cross hybridization and eliminates the need for laborious and costly hand emasculation and pollination. Several male sterile genes have been identified in watermelon, including the ms-1 gene. The ms-1 nuclear gene controls male sterility and, in plants with an ms-1 introgression, the normal development of anthers is hindered while female flower development is normal. The gene eliminates pollen production and results in an ideal female parent line for hybrid production.

The invention overcomes limitations in the prior art by providing methods and compositions for introgressing an ms-1 recessive allele into elite watermelon lines, permitting efficient production of hybrid seed. Commercial watermelon hybrids can be diploid and triploid. The diploid hybrids are produced from two diploid inbred parent lines while the triploid hybrids use a female tetraploid line and a male diploid parent line. The ms-1 recessive allele can be introgressed into the female diploid or tetraploid line.

The present invention provides compositions and methods for the introgression of the ms-1 allele into elite watermelon lines. The methods and compositions allow the use of marker assisted selection (MAS). In particular, genomic regions, alleles, polymorphic nucleic acids, and linked markers have been identified that are associated with male sterility in watermelon. A genetic map of the ms-1 gene was constructed. In one example, a segregating population from the cross of WSB-45-101S×SVR14227703 was developed, and phenotypic and genotypic data for 250 F2 individuals was collected. A linkage map was constructed, which consisted of 240 SNP markers and had a total of 20 linkage groups and total length of 1514.3 cM. A genomic region associated with a male sterile phenotype was identified at watermelon linkage group 2, between SNP markers NW0249314 (SEQ ID NO:1)/NW0249599 (SEQ ID NO: 6) (colocalized) and NW0250301 (SEQ ID NO: 78). NW0250301 is the most closely linked marker located 16.3 cM downstream of the ms-1 gene. In a further example, the ms-1 gene was mapped on linkage group 2 within the interval of the SNP markers NCLAN009404570 (SEQ ID NO: 28) and NCLAN009405170 (SEQ ID NO: 59), corresponding to about 150 kb on chromosome 6.

The present invention represents a significant advantage by providing genomic regions, alleles, polymorphic nucleic acids, and linked markers that are associated with male sterility in watermelon, methods of using such for the production or identification of watermelon plants comprising male sterility and watermelon plants produced by the methods wherein the watermelon plants comprise at least a first introgressed locus conferring male sterility. In accordance with the invention, the introgressed locus may be newly introgressed into a given genomic background of a specific variety or cultivar. Certain embodiments provide methods of detecting in a watermelon plant a genotype associated with male sterility. Other embodiments provide methods of identifying and selecting a watermelon plant comprising in its genome a genotype associated with male sterility. Further embodiments provide methods of producing a watermelon plant that comprises in its genome at least one introgressed locus associated with male sterility and methods for introgressing such an allele into a watermelon plant. Watermelon plants and parts thereof made by any of said methods are also provided for, as well as polymorphic nucleic acid sequences that may be used in the production and identification of such plants.

The markers associated with male sterility provided herein are useful for a variety of methods which utilize genotyping; the availability of markers reduce costs and unreliability associated with phenotyping assays. As an example, seeds or seedlings may be tested for the presence of marker alleles associated with the male sterility phenotype prior to sowing or transplanting, allowing selection and planting or transplanting of only male sterile seeds or seedlings for the female parent of a hybrid. The use of the markers disclosed herein results in seed production with up to 100% hybrid seed by reducing the risk of self pollination in a production field and also reduces or eliminates the presence of parent (non-hybrid) seed in a seed bag. Additionally, use of these markers can improve production capacity in a field. Planting only male sterile seed or plants of the female hybrid parent line provides improvement over the current method which includes planting, waiting until flowers develop and then passing over the field to rogue fertile female plants. The elimination of fertile female plants decreases labor input and resource costs. Further, breeding programs can be designed to specifically drive the frequency of specific favorable phenotypes by targeting particular genotypes. Fidelity of these associations may be monitored continuously to maintain predictive ability and informed breeding decisions. For example, markers may be used to identify and select the heterozygous condition of the ms-1 locus in progeny of a cross so that the trait can be conferred through a pedigree.

In accordance with the invention, one of skill in the art may identify a candidate germplasm source possessing male sterility as described herein, but which is lacking one or more traits which the plant breeder seeks to have in a variety or parent line thereof. The techniques of the invention may be used to identify male sterile phenotypes by utilizing genetic markers associated with the phenotype. Alternatively, such techniques may employ phenotypic assays to identify desired plants either alone or in combination with genetic assays.

Markers, including those described herein, may be assayed through the use of an automated, high-throughput, nondestructive seed sampling method as, for example, described in U.S. Pat. No. 8,076,076, incorporated herein by reference in its entirety. Briefly, the method comprises providing a population of seeds, removing a tissue sample comprising cells with nucleic acids from each seed in the population, analyzing the nucleic acids extracted from each seed for the presence of at least one genetic marker indicating the presence of a male-sterile gene, selecting seeds from the population based upon the presence of the male-sterile marker, and cultivating a fertile plant from the seed. The method additionally includes receiving and orienting the individual seeds, while preserving the germination viability of each seed, at an orientation subsystem of the automated seed processing system. The method further includes removing a tissue sample from the individual seeds, while preserving the germination viability of each seed, at a sampling subsystem of the automated seed processing system. Still further, the method includes depositing each seed into a selected well in a selected one of a plurality of seed collection trays after the seed has had a tissue sample removed and depositing each tissue sample into a selected well in a selected one of a plurality of sample collection trays, utilizing a seed and sample transport subsystem of the automated seed processing system. The method further includes storing in a database the selected well in the selected sample collection tray into which each sample was deposited and the selected well in the selected seed collection tray into which each corresponding sampled seed was deposited, such that each sample and corresponding seed from which the sample was removed can be tracked to pre-select seeds of interest.

Generally, watermelon sex expression can be divided into qualitative categories as being monoecious (separate male and female flowers on the same plant), andromonoecious (separate male and hermaphrodite flowers on the same plant), and trimonoecious (separate male, female and hermaphrodite flowers on the same plant).

In accordance with the invention, male sterility refers to the failure of plants to produce functional anthers, pollen, or male gametes, and/or any and all combinations thereof that one or more breeder, grower, or consumer may find advantageous for certain applications. Several male sterility genes have been identified in watermelon, including the ms-1 gene. The male sterility trait has been shown to be controlled by the genomic regions identified herein, and this trait may be introgressed into desired genetic backgrounds using the methods of the invention.

The present invention relates to watermelon genomic regions, polymorphic nucleic acids, and alleles associated with male sterility. This trait is important during the production of hybrid watermelon plants, which are produced by crossing a seed parent plant with a pollen parent plant. Typically, a female inbred parent line and a pollen donor (male) inbred line are crossed to produce a given commercial hybrid. For example, hybrid watermelon can be produced by crossing a diploid parent plant with a tetraploid parent plant or by crossing two diploid parent plants. Male sterility is important for hybrid seed production as it avoids the need for controlled pollination.

The genomic regions, polymorphic nucleic acids, and alleles of the present invention allow production of watermelon plants with decreased frequency of anthers on female flowers of seed parent inbred plants during hybrid seed production, thereby resulting in an increase in percent hybridity of the produced seed (less selfed seed). The present invention therefore relates to markers and genomic regions linked to male sterility and methods of use thereof in order to select parent lines that would better serve as seed parents for hybrid production.

The invention provides for the introgression of at least a first locus conferring male sterility into a given genetic background. Successful watermelon production depends on attention to various horticultural practices. These include soil management with special attention to proper fertilization, crop establishment with appropriate spacing, weed control, the introduction of bees or other insects for pollination, irrigation, pest management, and, if producing fruit from triploid plants, a suitable pollen source for producing seedless (triploid) watermelon. Watermelon flower size and shape; rind color, thickness and toughness; sex expression; flesh color, texture, and sugar content; and freedom from fruit defects are all important characteristics to be considered in selection of watermelon varieties.

Watermelon crops can be established from seed or from transplants. Transplanting can result in an earlier crop compared with a crop produced from direct seeding. When a grower wants to raise a seedless fruited crop, transplanting can be preferred. Transplanting helps achieve complete plant stands rapidly, especially where higher seed costs, as with triploid seeds, make direct-seeding risky.

Watermelon breeders are challenged with anticipating changes in growing conditions, new pathogen pressure, and changing consumer preferences. With these projections, a breeder will attempt to create new cultivars that will fit the needs of growers, shippers, retailers, and consumers. Thus, the breeder is challenged to combine, in a single genotype, as many favorable attributes as possible.

Genomic Region, Polymorphic Nucleic Acids, and Alleles Associated with Male Sterility in Watermelon Applicants have identified genomic regions, alleles, polymorphic nucleic acids, linked markers, and the like that when present in certain allelic forms are associated with watermelon male sterility.

A genomic region associated with a male sterile phenotype was identified at watermelon linkage group 2, flanked by loci NW0249314 (SEQ ID NO: 1)/NW0249599 (SEQ ID NO: 6 (colocalized) and NW0250301 (SEQ ID NO: 78). Another genomic region associated with a male sterile phenotype was identified at watermelon linkage group 2 (LG2), flanked by loci NCLAN009404570 (SEQ ID NO: 28) and NCLAN009405170 (SEQ ID NO: 59).

Certain of the various embodiments of the present disclosure thus utilize one or more polymorphic nucleic acid markers or alleles located in one or more of these regions or subregions on LG2. For example, NW0250301 (SEQ ID NO: 78) is a closely linked marker located 16.3 cM downstream of the ms-1 gene.

The above markers and allelic states are exemplary. One of skill in the art would recognize how to identify watermelon plants with other polymorphic nucleic acid markers and allelic states thereof related to watermelon male sterility consistent with the present disclosure. One of skill in the art would also know how to identify the allelic state of other polymorphic nucleic acid markers located in the genomic region(s) or linked to the QTL or other markers identified herein, to determine their association with watermelon male sterility.

Watermelons are natural diploids, having their chromosomes arranged in pairs. Watermelon plants, however, can undergo a duplication of their entire set of chromosomes and exist as tetraploids. While it is uncommon for watermelons to produce spontaneous tetraploids, this process can be routinely produced in the laboratory using cell biology techniques. Triploid seeds can be produced by crossing a tetraploid parent by a diploid parent. When triploid plants are grown, seed formation in the fruit aborts because of the ploidy level differences, resulting in seedless fruits.

In certain embodiments of methods of the invention, a diploid (female) parent plant is homozygous for a polymorphic nucleic acid marker allele associated with the male sterile phenotype. The diploid (female) parent is crossed with another diploid parent lacking the polymorphic nucleic acid marker allele associated with the male sterile phenotype to produce diploid hybrid progeny. This results in one copy of the polymorphic marker allele associated with the male sterile phenotype (from the diploid female parent) and one allele not associated with the male sterile phenotype (from the diploid male parent) in the diploid hybrid. Alternatively, in certain embodiments of methods of the invention, a tetraploid parent plant is homozygous for a polymorphic nucleic acid marker allele associated with the male sterile phenotype. The tetraploid parent is crossed with a diploid lacking the polymorphic nucleic acid marker allele associated with the male sterile phenotype, to produce triploid hybrid progeny. This results in two copies of the polymorphic marker allele associated with the male sterile phenotype (from the tetraploid parent) and one allele not associated with the male sterile phenotype (from the diploid parent) in the triploid hybrid.

Certain embodiments of the invention contemplate the use of dihaploidization to produce an inbred line. A haploid plant has only one copy of each chromosome instead of the normal pair of chromosomes in a diploid plant. Haploid plants can be produced, for example, by treating with a haploid inducer. Haploid plants can be subjected to treatment that causes the single copy chromosome set to double, producing a duplicate copy of the original set. The resulting plant is termed a "double-haploid" and contains pairs of chromosomes that are generally in a homozygous allelic state at any given locus. Dihaploidization can reduce the time required to develop new inbred lines in comparison to developing lines through successive rounds of backcrossing.

One of skill in the art would understand that polymorphic nucleic acids that are located in the genomic regions identified herein may be used in certain embodiments of the methods of the invention. Given the genomic regions and polymorphic markers identified herein, additional markers located either within or near a genomic region described herein that are associated with the phenotype can be obtained by typing new markers in various germplasm. The genomic region and polymorphic markers identified herein can also be mapped relative to any publicly available physical or genetic map to place the region described herein on such map. One of skill in the art would also understand that additional polymorphic nucleic acids that are genetically linked to the genomic region associated with a male sterile phenotype and that map within 40 cM, 20 cM, 10 cM, 5 cM, or 1 cM of the genomic region or the markers associated with a male sterile phenotype may also be used.

Introgression of a Genomic Locus Associated with Male Sterility

Marker-assisted introgression involves the transfer of a chromosomal region defined by one or more markers from a first germplasm to a second germplasm. Offspring of a cross that contain the introgressed genomic region can be identified by the combination of markers characteristic of the desired introgressed genomic region from a first germplasm (e.g. male sterile phenotype germplasm) and both linked and unlinked markers characteristic of the desired genetic background of a second germplasm.

Flanking markers that identify a genomic region associated with a desired sex expression phenotype can include any loci described herein on linkage group 2 (LG2), and those that identify sub-regions thereof can include any loci or loci intervals described herein on LG2.

For example, flanking markers that identify a genomic region or subregion include those defined by loci NW0249314 (SEQ ID NO: 1) and NW0250301 (SEQ ID NO: 78) on LG2 or within 15 cM thereof, or defined by loci NCLAN009404570 (SEQ ID NO: 28) and NCLAN009405170 (SEQ ID NO: 59) on LG2 or within 15 cM thereof.

In further embodiments, markers associated with a male sterile phenotype are: NW0249314 (SEQ ID NO: 1) and NW0250301 (SEQ ID NO: 78) on LG2 or flanked by loci NCLAN009404570 (SEQ ID NO: 28) and NCLAN009405170 (SEQ ID NO: 59) on LG2. In further embodiments, markers include NW0249314 (SEQ ID NO: 1), NW0249599 (SEQ ID NO: 6), NW0250496 (SEQ ID NO: 7), NW0249312 (SEQ ID NO: 12), NW0251153 (SEQ ID NO: 17), NW0248249 (SEQ ID NO: 22), NW0251130 (SEQ ID NO: 23), NCLAN009404570 (SEQ ID NO: 28), NCLAN009584571 (SEQ ID NO: 33), NCLAN009490296 (SEQ ID NO: 38), NCLAN009490491 (SEQ ID NO: 43), NCLAN009491448 (SEQ ID NO: 48), NW0251340 (SEQ ID NO: 53), NCLAN009490864 (SEQ ID NO: 54), NCLAN009405170 (SEQ ID NO: 59), NW0248760 (SEQ ID NO: 64), NCLAN009104771 (SEQ ID NO: 65), NW0248489 (SEQ ID NO: 70), NW0249128 (SEQ ID NO: 71), NW0251464 (SEQ ID NO: 72), NW0248953 (SEQ ID NO: 73), or NW0250301 (SEQ ID NO: 78). In certain embodiments, the marker is NCLAN009584571 (SEQ ID NO: 33). Exemplary markers provided by the invention are shown in Table 1.

TABLE 1

Markers associated with male sterility in watermelon.

| Marker | LG | Genetic Position (cM) | Allele of WT/fertile phenotype | Allele of male sterile parent/phenotype | DNA Sequence (SEQ ID NO) | Probe VIC Sequence (SEQ ID NO) | Probe FAM Sequence (SEQ ID NO) | Primer F Sequence (SEQ ID NO) | Primer R Sequence (SEQ ID NO) |
|---|---|---|---|---|---|---|---|---|---|
| NW0249314 | 2 | 39.92 | C | T | 1 | 2 | 3 | 4 | 5 |
| NW0249599 | 2 | 39.92 | C | T | 6 | | | | |
| NW0250496 | 2 | 43.44 | C | T | 7 | 8 | 9 | 10 | 11 |
| NW0249312 | 2 | 49.9 | G | A | 12 | 13 | 14 | 15 | 16 |
| NW0251153 | 2 | 59.39 | C | A | 17 | 18 | 19 | 20 | 21 |
| NW0248249 | 2 | 73.15 | | | 22 | | | | |
| NW0251130 | 2 | 80.02 | T | A | 23 | 24 | 25 | 26 | 27 |
| NCLAN009404570 | 2 | 80.96 | G | T | 28 | 29 | 30 | 31 | 32 |
| NCLAN009584571 | 2 | 82.03 | GTTTCAGTTC (SEQ ID NO: 83) | * | 33 | 34 | 35 | 36 | 37 |
| NCLAN009490296 | 2 | 82.05 | C | G | 38 | 39 | 40 | 41 | 42 |
| NCLAN009490491 | 2 | 82.05 | C | T | 43 | 44 | 45 | 46 | 47 |
| NCLAN009491448 | 2 | 82.46 | G | C | 48 | 49 | 50 | 51 | 52 |
| NW0251340 | 2 | 83 | 5 | | 53 | | | | |
| NCLAN009490864 | 2 | 83.16 | G | A | 54 | 55 | 56 | 57 | 58 |
| NCLAN009405170 | 2 | 83.67 | G | A | 59 | 60 | 61 | 62 | 63 |
| NW0248760 | 2 | 100.93 | | | 64 | | | | |
| NCLAN009104771 | 2 | 102.4 | A | G | 65 | 66 | 67 | 68 | 69 |
| NW0248489 | 2 | 115.84 | C | A | 70 | | | | |
| NW0249128 | 2 | 120.96 | G | C | 71 | | | | |
| NW0251464 | 2 | 122.47 | G | A | 72 | | | | |
| NW0248953 | 2 | 131.69 | T | A | 73 | 74 | 75 | 76 | 77 |
| NW0250301 | 2 | 134.25 | | | 78 | 79 | 80 | 81 | 82 |

Flanking markers that fall on both the telomere proximal end and the centromere proximal end of any of these genomic intervals may be useful in a variety of breeding efforts that include, but are not limited to, introgression of genomic regions associated with a male sterile phenotype into a genetic background comprising markers associated with germplasm that ordinarily contains a genotype associated with another phenotype.

Markers that are linked and either immediately adjacent or adjacent to the identified male sterile phenotype genomic region that permit introgression of the genomic region in the absence of extraneous linked DNA from the source germplasm containing the genomic region are provided herein. Those of skill in the art will appreciate that when seeking to introgress a smaller genomic region associated with a male sterile phenotype described herein, that any of the telomere proximal or centromere proximal markers that are immediately adjacent to a larger genomic region associated with a male sterile phenotype can be used to introgress that smaller genomic region.

A marker within about 40 cM of a marker associated with a male sterile phenotype described herein may be useful in a variety of breeding efforts that include, but are not limited to, introgression of genomic regions associated with a male sterile phenotype into a genetic background comprising markers associated with germplasm that ordinarily contains a genotype associated with another phenotype. For example, a marker within 40 cM, 20 cM, 15 cM, 10 cM, 5cM, 2 cM, or 1 cM of a marker associated with a male sterile phenotype or marker described herein can be used for marker-assisted introgression of a male sterile phenotype.

A marker within about 40 cM of a male sterile phenotype marker on LG2 described herein can be used for marker-assisted introgression of a male sterile phenotype. As described above, a male sterile phenotype marker on LG2 can include NW0250301 (SEQ ID NO: 78).

Watermelon plants or germplasm comprising an introgressed region that is associated with a male sterile phenotype wherein at least 10%, 25%, 50%, 75%, 90%, or 99% of the remaining genomic sequences carry markers characteristic of plant or germplasm that otherwise or ordinarily comprise a genomic region associated with another phenotype, are thus provided. Furthermore, watermelon plants comprising an introgressed region where closely linked regions adjacent and/or immediately adjacent to the genomic regions, QTL, and markers provided herewith that comprise genomic sequences carrying markers characteristic of watermelon plants or germplasm that otherwise or ordinarily comprise a genomic region associated with the phenotype are also provided.

Development of Male Sterile Watermelon Varieties

Male sterility in watermelon is important in terms of production of $F_1$ hybrid plants, and has significance to growers, processors, retailers, and customers. The present invention discloses the identification of genomic regions and alleles associated with male sterility, as well as single nucleotide polymorphism (SNP) markers genetically linked to and predictive of such loci that can be used for the tracking and introgression of male sterile traits into germplasm, such as by marker-assisted selection and/or marker-assisted backcrossing.

The invention thus allows the tracking and introduction of any of the genetic regions or markers identified herein into a given genetic background. One of ordinary skill will understand that a male sterile phenotype can be introgressed from one genotype to another using a primary locus described herein via marker assisted selection. Accordingly, a germplasm source can be selected that has a male sterile phenotype. A breeder can use the markers identified herein to select for male sterility or track male sterility during breeding using marker assisted selection for the region described herein. Provided with the present disclosure, one of ordinary skill can introduce male sterility into any genetic background.

For example, using the markers described herein, seed can be genotyped for the ms-1 markers of the present invention in order to select sterile plants for hybrid seed production. This method yields 100% hybridity in seed lot production, and reduces or eliminates parent (non-hybrid) seed contamination. This results in improved production capacity in the field, and represents an improvement over conventional methods of planting which involve selection of plants based on phenotype and roguing of fertile plants. Moreover, marker-assisted selection allows selection of the heterozygous state for breeding.

Thus, the genetic regions and markers identified herein can be used for marker assisted selection for male sterility in watermelon. This discovery of male sterility markers will facilitate the development of watermelon having a male sterile phenotype.

For most breeding objectives, commercial breeders work within germplasm that is "cultivated type" or "elite." This germplasm is easier to breed because it generally performs well when evaluated for horticultural performance. However, the performance advantage a cultivated germplasm provides is sometimes offset by a lack of allelic diversity. Breeders generally accept this tradeoff because progress is faster when working with cultivated material than when breeding with genetically diverse sources.

In contrast, when a breeder makes either intra-specific crosses, or inter-specific crosses, a converse trade off occurs. In these examples, a breeder typically crosses cultivated germplasm with a non-cultivated type. In such crosses, the breeder can gain access to novel alleles from the non-cultivated type, but may have to overcome the genetic drag associated with the donor parent. Because of the difficulty with this breeding strategy, this approach often fails because of fertility and fecundity problems. The difficulty with this breeding approach extends to many crops, and is exemplified with an important disease resistant phenotype that was first described in tomato in 1944 (Smith, *Proc. Am. Soc. Hort. Sci.* 44:413-16). In this cross, a nematode disease resistance was transferred from *L. peruvianum* (PI128657) into a cultivated tomato. Despite intensive breeding, it was not until the mid-1970s that breeders could overcome the genetic drag and release successful lines carrying this trait. Even today tomato breeders deliver this disease resistance gene to a hybrid variety from only one parent.

In watermelon, the plant introduction (PI) accessions are typically lines that produce fruits with undesirable production and eating qualities. Even though these lines have poor horticultural qualities, some watermelon breeders attempt to breed with these PI lines because they can potentially contain novel alleles. The process of introgressing novel resistance genes from the PI lines into acceptable commercial types is a long and often arduous process. This process can be difficult because the trait may be polygenic, or have low heritability, or have linkage drag or some combination thereof.

Some phenotypes are determined by the genotype at one locus. These simple traits, like those studied by Gregor Mendel, fall in discontinuous categories such as green or yellow seeds. Other variation observed in nature, however, is continuous, like yield in field corn, or human blood pressure. Unlike simply inherited traits, continuous variation can be the result of polygenic inheritance. Loci that affect continuous variation are referred to as QTLs. Variation in the phenotype of a quantitative trait is the result of the allelic composition at the QTLs and the environmental effect. The heritability of a trait is the proportion of the phenotypic variation attributed to the genetic variance. This ratio varies between 0 and 1.0. Thus, a trait with heritability near 1.0 is not greatly affected by the environment. Those skilled in the art recognize the importance of creating commercial lines with high heritability horticultural traits because these cultivars will allow growers to produce a crop with uniform market specifications.

Molecular Assisted Breeding Techniques

Genetic markers that can be used in the practice of the present invention include, but are not limited to, Restriction Fragment Length Polymorphisms (RFLP), Amplified Fragment Length Polymorphisms (AFLP), Simple Sequence Repeats (SSR), simple sequence length polymorphisms (SSLPs), Single Nucleotide Polymorphisms (SNP), Insertion/Deletion Polymorphisms (Indels), Variable Number Tandem Repeats (VNTR), and Random Amplified Polymorphic DNA (RAPD), isozymes, and others known to those skilled in the art. Marker discovery and development in crops provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) $Genomics$, 8(2), 271-278), denaturing gradient gel electrophoresis (Myers (1985) EPO 0273085), or cleavage fragment length polymorphisms (Life Technologies, Inc., Gathersberg, Md. 20877), but the widespread availability of DNA sequencing machines often makes it easier to simply sequence amplified products directly. Once the polymorphic sequence difference is known, rapid assays can be designed for progeny testing, typically involving some version of PCR amplification of specific alleles (PASA, Sommer, et al. (1992) $Biotechniques$ 12(1), 82-87), or PCR amplification of multiple specific alleles (PAMSA, Dutton and Sommer (1991) $Biotechniques$, 11(6), 700-7002).

As a set, polymorphic markers serve as useful tools for assaying plants to determine the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a watermelon plant a genotype associated with male sterility, identify a watermelon plant with a genotype associated with male sterility, and to select a watermelon plant with a genotype associated with male sterility. In certain embodiments of methods of the invention, polymorphic nucleic acids can be used to produce a watermelon plant that comprises in its genome an introgressed locus associated with male sterility. In certain embodiments of the invention, polymorphic nucleic acids can be used to breed progeny watermelon plants comprising a locus associated with male sterility.

Certain genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with a male sterile phenotype.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201,184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613; 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800, 944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616,464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates. If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

The markers to be used in the methods of the present invention may be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs.

Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which watermelon plants can be regenerated, plant calli, plant clumps and plant cells that are intact in plants or parts of plants such as pollen, flowers, seeds, leaves, stems, and the like.

As used herein, the term "male sterility" refers to the failure of plants to produce functional anthers, pollen, or male gametes, and can be cytoplasmic, genetic, or both.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "Quantitative Trait Locus (QTL)" is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, the term "introgressed," when used in reference to a genetic locus, refers to a genetic locus that has been introduced into a new genetic background, such as through backcrossing. Introgression of a genetic locus can thus be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked," when used in the context of nucleic acid markers and/or genomic regions, means that the markers and/or genomic regions are located on the same linkage group or chromosome such that they tend to segregate together at meiosis.

As used herein, the term "maturity" means maturity of fruit development. Maturity indicates the time a watermelon fruit is ready to be harvested. In watermelon, the maturity comes associated with changes in flesh color and sugar content.

As used herein, the term "denoting" when used in reference to a plant genotype refers to any method whereby a plant is indicated to have a certain genotype. This includes any means of identification of a plant having a certain genotype. Indication of a certain genotype may include, but is not limited to, any entry into any type of written or electronic medium or database whereby the plant's genotype is provided. Indications of a certain genotype may also include, but are not limited to, any method where a plant is physically marked or tagged. Illustrative examples of physical marking or tags useful in the invention include, but are not limited to, a barcode, a radio-frequency identification (RFID), a label, or the like.

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

EXAMPLES

The following disclosed embodiments are merely representative of the invention which may be embodied in various forms. Thus, specific structural, functional, and procedural details disclosed in the following examples are not to be interpreted as limiting.

Example 1

A segregating population was developed from a cross of WSB-45-101S×SVR14227703 and was used for mapping of the ms-1 gene; WSB-45-101S is a diploid Sugar Baby-type red flesh watermelon (a single male sterile, "MS", inbred plant of this genotype was selected) and SVR14227703 is a hybrid developed from the cross of WSB-142-1603 by BR618. Two hundred and fifty F2 individuals of the WSB-45-101S×SVR14227703 mapping population were transplanted for the collection of phenotypic data on male sterility and genotyped with multiple watermelon markers (Illumina GoldenGate OPA with 1202 validated SNP markers). Tissue of the 250 F2 individuals and the parental lines for genotyping was collected before transplanting the F2 plants in the field.

The F2 individuals were transplanted with sufficient spacing to allow for training of the vines and phenotyping at different time points during the vine development. Individual plants were scored as male sterile or male fertile after evaluating the length of the flower bud's peduncle, the flower bud size, the presence or absence of anthers and pollen in open flowers, and differences in anther development in flower buds. Plants were evaluated at three different time points throughout development to ensure that plants with male sterile flowers did not produce male fertile flowers at a later stage, and phenotypic scores were found to be in agreement for all individuals of the F2 segregating population.

JoinMap 4 software was used to develop a linkage map of the WSB-45-101S×SVR14227703 mapping population and map ms-1 in the watermelon genome. Briefly, linkage was calculated by independence LOD, ordering of linkage groups was conducted using the maximum likelihood algorithm, and genetic distances were estimated using the Haldane mapping function. The linkage map of WSB-45-101S× SVR14227703 consisted of 240 SNP markers, had a total of 20 linkage groups and map length of 1514.3 cM, as compared to the 11 linkage groups of the consensus map that has a length of 1892.7 cM.

The ms-1 gene mapped on linkage group 2 of the consensus map in the interval of the SNP markers NW0249314 (SEQ ID NO: 1)/NW0249599 (SEQ ID NO: 6) (colocalized) and NW0250301 (SEQ ID NO: 78). Due to the lack of polymorphic markers in this analysis in the interval of NW0249314/NW0249599 and NW0250301, which spans 94.4 cM on the consensus map, linkage group 2 split into two linkage groups in WSB-45-101S×SVR14227703. The most closely linked marker to ms-1 was NW0250301 which is located 16.3 cM downstream of the locus on linkage group 2. The location of ms-1 was confirmed using QTL Cartographer. A single QTL peak was identified in the watermelon genome above the LOD threshold of 2.5 using Composite Interval Mapping analysis, and was located near the marker NW0250301 (LOD=30.5).

The marker assay data of diverse watermelon germplasm carrying the ms-1 introgression was investigated for additional marker assays developed in the interval between NW0249314/NW0249599 and NW0250301 (FIG. 1). For all these lines, male sterility is maintained and the seed is harvested from male sterile (ms-1, ms-1) and male fertile (Ms-1, ms-1) plants in a 1:1 ratio. Consequently, these lines are expected to have heterozygous genotypes at the ms-1 locus since bulk seed samples were used for marker analysis. A region of heterozygosity was indeed identified for some of these lines near the SNP markers NW0248249 (SEQ ID NO: 22), NW0251340 (SEQ ID NO: 53), and NW0248760 (SEQ ID NO: 64). This is not far from the most likely region of ms-1 gene estimated from inference of genetic distance on the consensus map, which is highlighted in grey (FIG. 1).

Markers from this genomic region of linkage group 2 were selected to genotype a diverse panel of watermelon lines that were phenotyped on a plant basis. This panel includes 34 lines of 9 different market types (FIG. 1). Eight plants for each of these 34 lines that segregate for male sterility were transplanted in a randomized complete block (RCBD) design and tissue sampled. Phenotypic and genotypic data obtained confirmed marker-trait association in different market types and identified an informative marker in the proximity of ms-1 that accurately predicts the phenotype.

Example 2

A. Mapping

Using two F2 populations, WCS-146-21905/WNE-142-1204 (referred to as population 1) and WSB-45-101S/WCS-39-100 (referred to as population 2), the ms-1 gene was mapped between 78 (NW0251130; SEQ ID NO: 23) and 101.8 cM (NCLAN009104771; SEQ ID NO: 65). Using polymorphic markers in the gene region, a total of 1100 and 780 F2 plants were screened for recombinants in the gene region from population 1 and 2, respectively. A total of 281 recombinants were selected and phenotyped for male sterility. Additional markers were developed and used to genotype the identified recombinants. This analysis placed ms-1 between markers NW0251130 (SEQ ID NO: 23) and NCLAN009405170 (SEQ ID NO: 59) using a total of 4 recombinants.

An additional 203 BC plants derived from 30 BC families (segregating for male sterility as in a backcross) were phenotyped and genotyped with markers in the ms-1 region to confirm its location (FIG. 2). The analysis indicated that ms-1 is located between NCLAN009404570 (SEQ ID NO: 28) and NCLAN009405170 (SEQ ID NO: 59). Three recombinants were identified between ms-1 and NCLAN009404570 (SEQ ID NO: 28) and six recombinants were identified between ms-1 and NCLAN009405170 (SEQ ID NO: 59).

The data above shows that the ms-1 gene is located on LG 2 between NCLAN009404570 and NCLAN009405170.

B. Additional Fine Mapping

Figure 3:
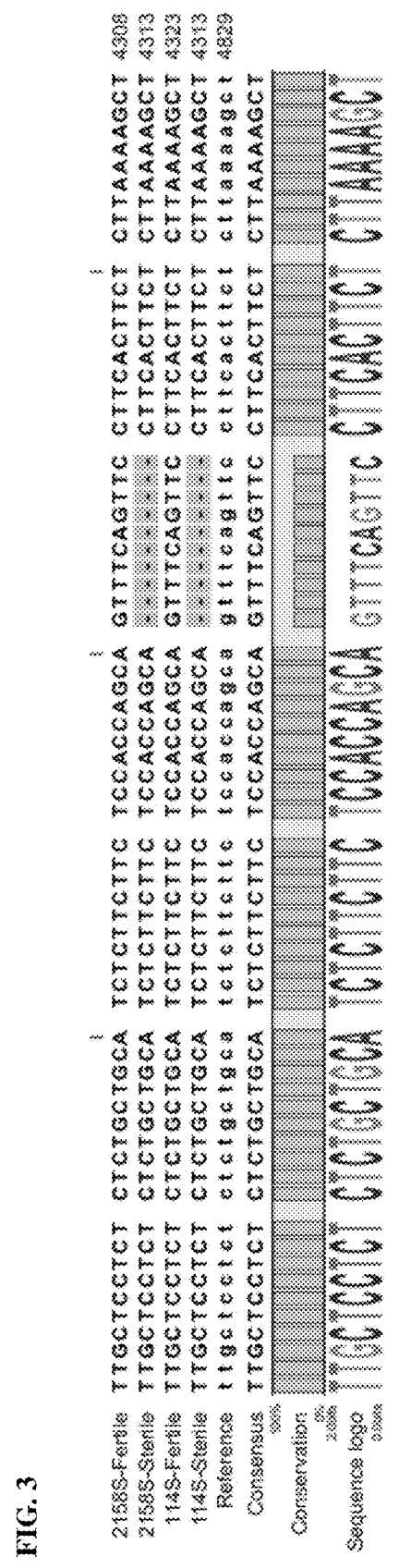

Two SNPs were converted into TaqMan markers (NCLAN009490491 [SEQ ID NO: 43] and NCLAN009490296 [SEQ ID NO: 38]) and used for fine mapping. These SNPs were not present in all sterile families (only polymorphic in three families). An indel (FIG. 3) was converted into the TaqMan marker NCLAN009584571 (SEQ ID NO: 33; 82.03cM) for analysis on the fine mapping panel and in a larger panel of sterile lines and elite germplasm.

A total of 1223 plants from 5 BC1 families segregating for male sterility were analyzed with markers flanking the ms-1 gene. The markers were NCLAN009404570 (SEQ ID NO: 28) and NCLAN009405170 (SEQ ID NO: 59) and 4 additional interstitial markers: NCLAN009490296 (SEQ ID NO: 38), NCLAN009490491 (SEQ ID NO: 43); NCLAN009491448 (SEQ ID NO: 48); NCLAN009490864 (SEQ ID NO: 54). A total of 74 recombinants were identified. Based on the distribution of the recombination events, 56 recombinants were selected and phenotyped.

A total of 16 recombinants were identified between ms-1 and NCLAN009404570 (SEQ ID NO: 28) and 10 between ms-1 and NCLAN009491448. These recombinants strongly indicate that ms-1 is between NCLAN009404570 (81 cM) and NCLAN009491448 (SEQ ID NO: 48; 82.46 cM) on LG2, corresponding to about 80 kb on chromosome 6.

After additional targeted re-sequencing, the mapping panel was analyzed with the marker NCLAN009584571 (SEQ ID NO: 33). The marker was confirmed as being closely linked to ms-1, but did not reduce the interval of 81-82.46 cM.

C. Accuracy Analysis

Regions in the interval containing ms-1 were targeted for re-sequencing using the parents of the two mapping populations as well as fertile and sterile plants from five of the 30 male sterility families mentioned above (segregating for male sterility as in backcross). The regions were selected for re-sequencing using two criteria: (1) within a gene and/or (2) presenting informative SNP based on the whole genome re-sequenced lines (fixed in all 9 fertile lines with data and heterozygote in 1 line segregating for male sterility). One single SNP, NCLAN009584571 (SEQ ID NO: 33) was found completely associated with the phenotype in the re-sequencing panel.

An accuracy panel was assembled from a diverse set of 34 male sterile and 46 fertile lines. For the 34 male sterile families, eight plants from each family were transplanted into the field for phenotyping of individual plants. Plants were phenotyped until there were at least three consistent ratings on sequential time points. TM markers in the interval (81-82.5 cM) were run on the panel.

To analyze the male sterile lines it was first determined whether the marker was segregating with the phenotype, indicating if the marker will be informative for differentiating male sterile and fertile plants within the family (% of families that marker is segregating; Table 2). The marker NCLAN009405170 (SEQ ID NO: 59) is segregating in all but three of the families; however the marker NCLAN009584571 (SEQ ID NO: 33) is segregating in all families. Secondly, the fertile homozygous allele calls were derived for each of the male sterile families. The frequency of the sterile allele was then calculated in the sterile and fertile lines. The analysis of an accuracy panel showed that NCLAN009584571 is highly associated with the ms-1 phenotype (Table 2).

TABLE 2

Allele frequency analysis for the presence of the sterile allele in sterile and fertile lines.

| Group | N | Marker | Position (LG2) 81.02 NCLAN009404570 | 82.03 NCLAN009584571 | 82.05 NCLAN009490296 | 84.2 NCLAN009405170 |
|---|---|---|---|---|---|---|
| Sterile (S) Allele | | WAS-45-2158S | TT | ** | GG | AA |
| Sterile | 34 | S allele freq | 1.00 | 1.00 | 1.00 | 0.91 |
| Fertile - FS | 34 | S allele freq | 0.35 | 0.00 | 0.35 | 0.00 |
| Fertile - elite | 46 | | 0.46 | 0.00 | 0.48 | 0.00 |
| Fertile - all | 80 | | 0.41 | 0.00 | 0.43 | 0.00 |
| % of FS families that marker is het | 34 | | 0.65 | 1.00 | 0.68 | 0.91 |

The ms-1 gene has been mapped to a 1.5 cM interval between 81-82.5 cM on LG2. The marker NCLAN009584571 (SEQ ID NO: 33) is highly associated to the trait.

What is claimed is:

1. A method of determining the genotype associated with a male sterile phenotype of a watermelon plant or part thereof, the method comprising the steps of:
   (a) obtaining a sample of material from said plant or part thereof;
   (b) detecting in said sample the presence of at least a first polymorphism in or genetically linked to a locus that confers said male sterile phenotype, wherein said locus comprises SEQ ID NO: 33, and wherein said at least first polymorphism is located within 5 cM of said SEQ ID NO: 33;
   (c) identifying or selecting a plant comprising the male sterile phenotype;
   (d) crossing the plant of step (c) with a second watermelon plant, wherein said second watermelon plant lacks or is heterozygous for said locus that confers said male sterile phenotype;
   (e) collecting seed from the cross of step (d); and
   (f) growing progeny plants from the seed of step (e), thereby producing a watermelon plant comprising the male sterile phenotype compared to a plant lacking said polymorphism in or genetically linked to a locus that confers said male sterile phenotype.

2. A method of identifying a watermelon plant comprising a genotype associated with a male sterile phenotype, the method comprising the steps of:
   (i) detecting in said plant the presence of at least a first polymorphism in or genetically linked to a locus that confers said male sterile phenotype, wherein said locus comprises SEQ ID NO: 33, and wherein said at least first polymorphism is located within 5 cM of said SEQ ID NO: 33;
   (ii) selecting said watermelon plant from a population of watermelon plants based on the presence of said polymorphism;
   (iii) crossing the plant of step (ii) with a second watermelon plant, wherein said second watermelon plant lacks or is heterozygous for said locus that confers said male sterile phenotype;
   (iv) collecting seed from the cross of step (iii); and
   (v) growing progeny plants from the seed of step (iv), thereby producing a watermelon plant comprising the male sterile phenotype compared to a plant lacking said polymorphism in or genetically linked to a locus that confers said male sterile phenotype.

3. A method of introgressing an allele into a watermelon plant, the method comprising:
   (i) genotyping at least one watermelon plant in a population with respect to at least one polymorphism located in or genetically linked to a genomic region comprising SEQ ID NO: 33, wherein said polymorphism is within 5 cM of said SEQ ID NO: 33;
   (ii) selecting from the population at least one watermelon plant comprising at least one allele associated with a male sterile phenotype;
   (iii) crossing the plant of step (ii) with a second plant, wherein the second plant does not comprise said at least one allele associated with a male sterility phenotype;
   (iv) collecting seed from the cross of step (iii); and
   (v) growing progeny plants from the seed of step (iv), thereby producing a watermelon plant comprising said at least one allele associated with a male sterility phenotype.

* * * * *